United States Patent [19]

Kuroiwa et al.

[11] Patent Number: 4,584,398
[45] Date of Patent: Apr. 22, 1986

[54] ARGINYL-3-CARBOXY-4-HYDROXYANILIDE

[75] Inventors: Katsumasa Kuroiwa; Shuichi Nakatsuyama, both of Koriyama; Takeshi Nagasawa, Urawa, all of Japan

[73] Assignee: Nitto Boseki Co., Ltd., Fukushima, Japan

[21] Appl. No.: 697,333

[22] Filed: Feb. 1, 1985

[30] Foreign Application Priority Data

Feb. 10, 1984 [JP] Japan ................................. 59-21901

[51] Int. Cl.$^4$ ........................................... C07C 129/08
[52] U.S. Cl. .................................................. 562/439
[58] Field of Search ................... 562/439, 453; 560/39

[56] References Cited

U.S. PATENT DOCUMENTS

| 3,824,267 | 7/1974 | Ito et al. | 562/439 |
| 4,281,181 | 7/1981 | Nagasawa et al. | 562/453 |
| 4,450,105 | 5/1984 | Nagasawa et al. | 435/23 |

Primary Examiner—James H. Reamer
Attorney, Agent, or Firm—Bert J. Lewen; Henry Sternberg

[57] ABSTRACT

Novel arginyl-3-carboxy-4-hydroxyanilide of the formula

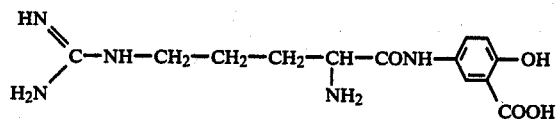

and acid addition salts thereof are of use as starting materials for preparing chromophoric and fluorescent substrates for measurement of enzyme activity.

1 Claim, No Drawings

ARGINYL-3-CARBOXY-4-HYDROXYANILIDE

The present invention relates to novel arginyl-3-carboxy-4-hydroxyanilide and acid addition salts thereof, which are useful as starting materials for preparing chromophonic and fluorescent substrates for measurement of enzyme activity.

The present inventors made a success of synthesis of novel arginyl-3-carboxy-4-hydroxyanilide represented by formula (I)

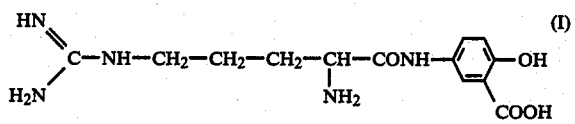

and further found that this novel compound is of great use as a starting material for synthesizing chromophoric and fluorescent substrates for measurement of enzyme activity, and accomplished the present invention.

The present compound is of use as a starting material for synthesizing substrate used in measurement of the activity of enzymes such as trypsin, urokinase, thrombin etc., which hydrolyze a basic amino acid specifically at the carboxylic position thereof. For example, compounds of the formula

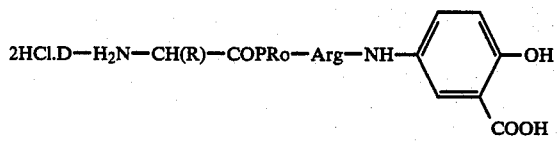

wherein R represents

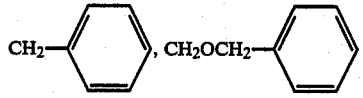

and the like, are of use as synthetic chromophoric substrates for measuring the activity of thrombin (see U.S. Pat. No. 4,450,105). These compounds were obtained in high yields under mild reaction conditions starting with the present compound, as shown in the Reference Example given below.

Arginyl-3-carboxy-4-hydroxyanilide according to the present invention is stable in the form of acid addition salts thereof. Examples of acids used therefor include mineral acids such as hydrochloric acid, sulfuric acid etc., and organic acids such as acetic acid, p-toluenesulfonic acid etc. Neutralization of the acid addition salts with alkali yields the free acid form.

The present aryinyl-3-carboxyl-4-hydroxyanilide was produced very simply as an acid addition salt thereof, as illustrated in the Example given below. That is, $N^\alpha$-tert-butyloxycarbonylarginine hydrochloride·hydrate and 3-carboxy-4-hydroxyaniline were subjected to dehydration-condensation by the mixed acid anhydride method which is well used in the peptide synthesis. Subsequently the protecting groups were removed under mild conditions using 2N hydrochloric acid-acetic acid to give arginyl-3-carboxyl-4-hydroxyanilide dihydrochloride.

The present arginyl-3-carboxy-4-hydroxyanilide and acid addition salts thereof are useful as starting materials for synthesizing chromophoric acid fluorescent peptides.

A process for preparing the present compound is illustrated concretely in the following Example and the use thereof as a starting material is also illustrated in the Reference Example given below.

EXAMPLE 115 g (0.35 mole) of $N^\alpha$-tert-butyloxycarbonyl-arginine hydrochloride monohydrate was dissolved in a solvent mixture of 420 ml of DMF and 45.5 ml (0.35 mole) of N-ethylmorpholine. Thereafter, the resulting solution was cooled to $-20° \sim 15°$ C., to which was added dropwise with stirring 47.8 g (0.35 mole) of isobutylchloroformate. After completion of the addition the reaction was continued for five minutes. Subsequently, to the reaction mixture was added dropwise while cooling and stirring a solution of 53.6 g (0.35 mole) of 3-carboxy-4-hydroxyaniline in a solvent mixture of 280 ml of DMF and 45.5 ml (0.35 mole) of N-ethylmorpholine. After completion of the addition the reaction was effected at $-5° \sim 0°$ C. for three hours, and then at room temperature for two hours.

After completion of the reaction, the insolubles were removed by filtration and the solvent was distilled off under reduced pressure. The residue was dissolved in 140 ml of methanol and 100 ml of n-butanol. To the resulting solution was added 1l of ethyl acetate. The mixture was in order washed three times with 750 ml of 5% cold hydrochloric acid saturated with sodium chloride and twice with 650 ml of saturated aqueous sodium chloride, and dried over anhydrous magnesium sulfate. The solvent was distilled off under reduced pressure to obtain 131.1 g of the brown residue. The residue was dissolved in 3l of methanol, 56 g of active carbon was added and stirred at room temperature for $3 \sim 4$ days for decolorization. The active carbon was removed by filtration and the filtrate was distilled completely under reduced pressure to obtain 101.4 g (yield 65%) of oily substance, $N^\alpha$-tert-butyloxycarbonyl-arginyl-3-carboxy-4-hydroxyanilide hydrochloride.

The oily substance was dissolved in 200 ml of methanol. To the solution was added 455.2 ml of 2N hydrochloric acid-acetic acid while cooling in ice and stirring, and the reaction was effected at room temperature for one hour to remove the $N^\alpha$ protecting group. After completion of the reaction 350 ml of isopropanol was added to the reaction mixture and the mixture was poured into 5.5 l of ethyl acetate. The precipitate formed was collected by filtration and dried under reduced pressure to obtain 78 g (yield 90%) of crystals of arginyl-3-carboxy-4-hydroxyanilide dihydrochloride. Melting point $217° \sim 225°$ C. (decomposition). $[\alpha]_D^{20} = +53.5°$ (c=1, water). Thin layer chromatography of the crystals using silica gel (n-butanol:acetic acid:water=4:1:5) showed a single spot. Rf=0.17.

Elementary analysis for $C_{13}H_{21}N_5O_4Cl_2 \cdot \frac{1}{2}CH_3COOH \cdot H_2O$

|  | C | H | N |
| --- | --- | --- | --- |
| Found (%): | 38.91 | 5.63 | 16.40 |
| Calc'd (%): | 39.08 | 5.86 | 16.28 |

Synthesis of D-phenylalanyl-prolyl-arginyl-3-carboxy-4-hydroxyanilide dihydrochloride from the product obtained above as a starting material is described by the following Reference Example.

REFERENCE EXAMPLE 40.0 g (0.11 mole) of tert-butyloxycarbonyl-D-phenylalanyl-proline was dissolved in a solvent mixture of 141 ml of DMF and 14.3 ml of N-ethylmorpholine, cooled to $-15°$ C. and 14.5 ml of isobutylchloroformate was added dropwise to the resulting solution while stirring. After completion of the addition the reaction was continued for five minutes, and then to the reaction mixture was added dropwise a solution of 42.0 g (0.11 mole) of arginyl-3-carboxy-4-hydroxyanilide dihydrochloride in a solvent mixture of 235 ml of DMF and 28.6 ml of N-ethylmorpholine. The reaction was effected at $-10°$ C. for three hours, and at room temperature for three hours. After completion of the reaction, the insolubles were removed by filtration and the solvent was distilled off under reduced pressure. The residue was dissolved in a small amount of methanol and 940 ml of ethyl acetate was added thereto. The mixture was washed twice with 560 ml of 5% cold hydrochloric acid saturated with sodium chloride, and then twice with 560 ml of saturated aqueous sodium chloride. After dehydrating and drying over anhydrous magnesium sulfate, the solvent was distilled off under reduced pressure. The residue was dissolved in methanol and ether added to precipitate crystals. The crystals were collected by filtration, and dried under reduced pressure to obtain 61.3 g (yield 80.8%) of crystals of tert-butyloxycarbonyl-D-phenylalanylprolyl-arginyl-3-carboxy-4-hydroxyanilide hydrochloride (II). M.P. 195°~198° C.

To 60 g (86.9 mmole) of the above crystals (II) was added a small amount of methanol and 260.7 ml of 2N hydrochloric acid-acetic acid added dropwise while cooling in ice and stirring. After completion of the addition the reaction was conducted at room temperature for one and a half hours. After completion of the reaction the reaction mixture was poured into 4.5 l of ether. The precipitate formed was collected by filtration and recrystallized from ethanol-methanol to obtain 39.2 g (yield 72.0%) of crystals of D-phenylalanyl-prolyl-arginyl-3-carboxy-4-hydroxyanilide hydrochloride. M.P. 210°~213° C. (decomposition). $[\alpha]_D^{20} = -109.0°$ (c=0.5, methanol). Thin layer chromatography of the crystals using silica gel (n-butanol:acetic acid:water=4:1:5) showed a single spot. Rf=0.29.

Elementary analysis

|  | C | H | N |
|---|---|---|---|
| Found (%): | 49.60 | 6.07 | 14.51 |
| Calc'd (%): | 49.85 | 6.13 | 14.53 |

What is claimed is:
1. Arginyl-3-carboxy-4-hydroxyanilide of formula (I)

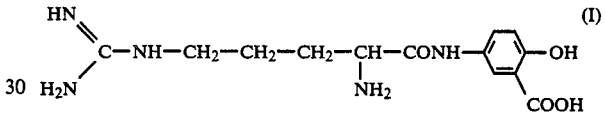

and acid addition salts thereof.

* * * * *